United States Patent [19]

Okumura et al.

[11] 3,969,375

[45] July 13, 1976

[54] METHOD OF MANUFACTURING SALT OF α-SULFOFATTY ACID ESTER

[75] Inventors: Osamu Okumura, Funabashi; Takenobu Sakatani, Chiba; Kazuo Ohbu; Masuzo Nagayama, both of Tokyo, all of Japan

[73] Assignee: Lion Fat & Oil Co., Ltd., Tokyo, Japan

[22] Filed: Nov. 18, 1974

[21] Appl. No.: 524,709

[30] Foreign Application Priority Data
Nov. 29, 1973  Japan............................. 48-134693

[52] U.S. Cl............................. 260/400; 260/481 R
[51] Int. Cl.².................... C11D 1/28; C07C 143/12
[58] Field of Search...................... 260/400, 481 R

[56] References Cited
UNITED STATES PATENTS

| | | | |
|---|---|---|---|
| 3,256,303 | 6/1966 | Stein et al. | 260/400 |
| 3,328,460 | 6/1967 | Van der Mey | 260/505 S |

Primary Examiner—Patrick P. Garvin
Attorney, Agent, or Firm—Woodhams, Blanchard and Flynn

[57] ABSTRACT

A neutralized product containing salt of α-sulfofatty acid ester in high concentration can be produced by the method comprising the steps of (1) sulfonating fatty acid ester by contacting a gaseous mixture of sulfur trioxide ($SO_3$) and an inert gas containing 1 – 15% by volume of $SO_3$ with a film of a fatty acid ester, said ester having the formula $RCH_2COOR'$ (wherein R is alkyl having 8 – 18 carbon atoms and R' is alkyl having 1 – 5 carbon atoms), under the conditions that the molar ratio of $SO_3$ to said fatty acid ester is in the range of 1.0 – 1.5, the temperature is in the range of 50° – 85°C and the time of contact is in the range of 0.5 – 30 seconds; (2) contacting a film of the reaction product obtained by step (1) into contact with said gaseous mixture, under the conditions of a temperature in the range of 95 – 150°C and a time of contact in the range of 3 – 120 seconds; and (3) instantly neutralizing the reaction product obtained by step (2) with a base selected from the group consisting of an aqueous solution of alkali metal hydroxide, ammonia water and ethanol amine while retaining the condition that the pH value is in the range of 6 – 10 and the temperature is less than 70°C. This neutralized product is usable as the active ingredient a detergent without subjecting it to any further treatment.

8 Claims, No Drawings

METHOD OF MANUFACTURING SALT OF α-SULFOFATTY ACID ESTER

BACKGROUND OF THE INVENTION

The present invention relates to a method of manufacturing a salt of an α-sulfofatty acid ester by sulfonating a saturated fatty acid ester and thereafter neutralizing the sulfonated ester. To be more precise, it relates to a method of manufacturing a light-colored salt of an α-sulfofatty acid ester useful as a surface active agent, in high yield.

Salts of α-sulfofatty acid ester to be obtained by sulfonating saturated fatty acid esters and neutralizing the sulfonated esters thereafter has various advantages such as, they possess not only a satisfactory hard water resistance but also an excellent wettability and are mild to the skin so that they are useful as detergents and wetting agents.

It is known that, when a saturated fatty acid is sulfonated and thereafter neutralized with sodium hydroxide, there can be produced sodium α-sulfofatty acid ester, disodium salt of α-sulfofatty acid and monosodium salt of α-sulfofatty acid as shown in the following:

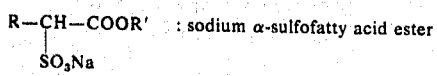 : sodium α-sulfofatty acid ester

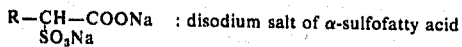 : disodium salt of α-sulfofatty acid

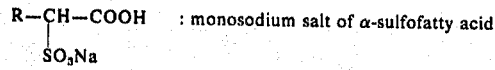 : monosodium salt of α-sulfofatty acid

The differences of the properties of sodium α-sulfofatty acid ester, disodium salt of α-sulfofatty acid and monosodium salt of α-sulfofatty acid are very great; for instance, as to the water solubility, that of sodium α-sulfofatty acid ester is about 100 times as high as that of the disodium salt of α-sulfofatty acid and is about 1,000 times as high as that of the monosodium salt of α-sulfofatty acid. Also, as to wettability, surface tension, solubilizability, detergency and foamability, sodium α-sulfofatty acid ester is by far superior to the disodium salt and monosodium salt thereof. This verifies the disodium salt of α-sulfofatty acid and monosodium salt of α-sulfofatty acid are unsuitable for use as surface active agents for detergent. Nevertheless, inasmuch as the solubilizability of sodium α-sulfofatty acid ester is superb, when sodium α-sulfofatty acid ester is present in an amount of not more than about 80% of the entire surface active agent, even when the remaining 20% or less consists of disodium salt of α-sulfofatty acid and monosodium salt of α-sulfofatty acid, said surface active agent can serve as the active ingredient of detergents. However, when the content of sodium α-sulfofatty acid ester is less than 80%, the detergency, solubilizability and so on decrease precipitously, rendering the surface active agent unfit for use as the active ingredient for detergents. That is, a surface active agent which fails to contain sodium α-sulfofatty acid ester to the extent of more than 80% is unusable as the active ingredient of detergents.

As to the reaction mechanism for sulfonating saturated fatty acid ester having the formula $RCH_2COOR'$ with $SO_3$, it is presumed that this sulfonation reaction progresses through two stages: the first stage where an adduct having the formula

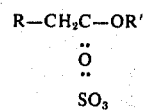

is formed at a high speed from saturated fatty acid ester and $SO_3$, and the second stage where in a rearrangement reaction of said adduct takes place to form α-sulfofatty acid ester having the formula

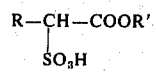

at a low speed. When the speed of forming this α-sulfofatty acid ester is compared with the speed of forming other anionic surface active agents, for instance, the speed of sulfonation of alkyl benzene, monoolefin or higher alcohol with an appropriate sulfonating agent such as sulfuric anhydride, fuming sulfuric acid or chlorosulfonic acid, the latter speed is very high and the sulfonation reaction is completed instantaneously upon contact with said sulfonating agent, while the former speed is so slow that a certain period of time is required for forming α-sulfofatty acid ester by rearrangement reaction of $SO_3$ adduct.

As method of sulfonating fatty acids or derivatives thereof, there have hitherto been known the batch process and the film process: the former is a process comprising effecting the sulfonation reaction by blowing diluted $SO_3$ gas into fatty acid or derivative thereof and then effecting 10 – 30 minutes' aging by raising the temperature to thereby complete the rearrangement reaction, wherein the aging reaction is indispensable. However, in the case of the batch process reaction, a very long time is required for completion of the entire reaction so that the product tends to be remarkably discolored and become unfit for use in detergents even when a bleaching process is applied thereto. Further, in the case of sulfonation of fatty acid derivatives, especially fatty acid esters thrugh the batch process, inasmuch as $SO_3$ is employed in excess, that is, the molar ratio of $SO_3$ to fatty acid ester is almost in the range of 1.0 – 1.5, when the reaction takes a long time, by the catalytic action of excess $SO_3$, the ester linkage or

is cut owing to the presence of a trifling amount of water, resulting in lowering of the yield of the principal product α-sulfofatty acid ester while producing α-sulfofatty acid amounting to more than 30%, so that the sulfonation product obtained through the batch process is unfit for use as the active ingredient for detergents.

Meanwhile, in the case of the method of sulfonating at a high temperature in the range of 95° – 150°C by the use of a film process type reactor such as taught in the specification for British Pat. No. 1145101, improvement of the color tone is admittedly observed as compared with the batch process, yet this method is defective in that, when it is applied to the sulfonation of saturated fatty acid esters and the reaction is effected by applying a high temperature from the outset, unlike the sulfonation of saturated fatty acid, the SO₃ adduct cannot be formed easily (cf. the foregoing description of the reaction mechanism) but the cutting of the ester linkage progresses as the principal reaction, so that not only does the rate of reaction lower to less than 90%, but also the yield of α-sulfofatty acid ester decreases to less than 80%.

As seen in the foregoing, in the case of sulfonating fatty acid esters, it has hitherto been difficult to obtain a sulfonation product having a satisfactory color and containing more than 80% of α-sulfofatty acid ester through either the batch process or the film process in the prior art.

Referring to the method of neutralization, the conventional method is to neutralize by adding the sulfonation product of the fatty acid ester to a highly alkaline aqueous solution (with pH value of more than 12). This conventional method, however, has been defective in that, the ester linkage of the α-sulfofatty acid ester is easily cut by hydrolysis, and when the temperature of neutralization is high, the speed of hydrolysis becomes high to further expedite the cutting of the ester linkage, resulting in a decrease of the yield of the α-sulfofatty acid ester The present invention has been accomplished as the result of a series of studies that aimed to overcome the foregoing drawbacks in the conventional methods of manufacturing salts of α-sulfofatty acid esters, and its object is to provide an improved method capable of producing a light-colored salt of α-sulfofatty acid esters useful as surface active agents.

SUMMARY OF THE INVENTION

The method of manufacturing a water-soluble salt of α-sulfofatty acid ester according to the present invention comprises: (1) the step of forming a flowing of sulfonation product by contacting a flowing of gaseous mixture of sulfur trioxide and an inert gas containing 1 – 15% by volume of sulfur trioxide with a downwardly flowing film of a fatty acid ester having by the formula RCH₂COOR' (wherein R is alkyl having 8 – 18 carbon atoms and R' is alkyl having 1 – 5 carbon atoms), under the conditions that the molar ratio of SO₃ to fatty acid ester is in the range of 1.0 – 1.5, the temperature is in the range of 50° – 85°C and the time of contact is in the range of 0.5 – 30 seconds; (2) the steps of contacting a film of said sulfonation product of step (1) into contact with a flow of said gaseous mixture step, under the condition that the temperature is in the range of 95° – 150°C and the time of contact is in the range of 3 – 120 seconds; and (3) the step of instantly neutralizing the heated flow of sulfonation product from step (2) with an aqueous solution of an alkali metal hydroxide, ammonia water or ethanol amine while retaining the condition that the pH value is in the range of 6 – 10 and the temperature is less than 70°C.

The fatty acid ester employed herein means substances having the formula RCH₂COOR' (wherein R is straight-chain or branched-chain alkyl having 8 – 18 carbon atoms, preferably 10 – 16 carbon atoms, and R' is straight-chain or branched-chain alkyl having 1 – 5 carbon atoms, preferably 1 – 2 carbon atoms); these substances may be derivatives obtained from natural fatty acid esters, products obtained by esterifying soap resulting from saponification of alcohol and further synthetic fatty acid esters derived by an improved oxo synthesis of α-olefin, that is to say, they are not limited to any particular ones. To give concrete examples of said substances, there are methyl laurate, ethyl laurate, propyl laurate, methyl palmitate, ethyl palmitate, methyl stearate, ethyl stearate, methyl hydrogenated tallow fatty acid ester, ethyl hydrogenated tallow fatty acid ester, methyl coco fatty acid ester, ethyl coco fatty acid ester, methyl hydrogenated palm fatty acid ester, ethyl hydrogenated palm fatty acid ester, etc. These fatty acid esters can be employed either independently or upon admixing two or more of them at optional ratio, but, in all cases, the iodine number of the starting fatty acid ester is desired to be less than 1.

As the reactor for use in the present invention, a continuous falling film type sulfonator is employed.

SO₃ is supplied in the state of a diluted gas. As the diluent gas, such inert gases as air, nitrogen, carbon dioxide, sulfur dioxide acid gas, etc. are usually employed. The concentration of SO₃ in the diluted gas is in the range of 1 – 15% by volume, preferably in the range of 2 – 10% by volume. The appropriate molar ratio of SO₃ to fatty acid ester is in the range of 1.0 – 1.5; when said molar ratio of SO₃ is less than 1.0, the rate of reaction of the fatty acid ester comes to be as low as less than 90% and its efficiency as the active ingredient for detergents is insufficient, while in the case where said molar ratio of SO₃ is more than 1.5, not only does the color of the product deteriorate but also the ester linkage

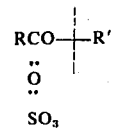

of SO₃ adduct

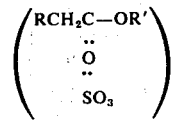

is cut in the presence of a trifling amount of water by the catalytic action of the excess SO₃, entailing a decrease in the yield of α-sulfofatty acid ester to less than 80% and its efficiency as the surface active agent is insufficient. This means that the reaction temperature and the time of contact have a very important effect on the yield and color of the α-sulfofatty acid ester, and accordingly, in order to secure a high yield of α-sulfofatty acid ester with a satisfactory color, the reaction temperature and the time of contact should be strictly regulated.

From this point of view, in the present invention, the sulfonation reaction process is divided into two stages, and for each stage, the reaction temperature and the time of contact are respectively specified. To be precise, on the occasion of sulfonating a fatty acid ester with SO₃, the reaction progresses at the first stage where fatty acid ester and SO₃ produce an adduct

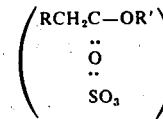

at a high speed and at the second stage where the rearrangement is effected at a low speed to convert said adduct into α-sulfofatty acid ester

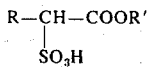

as set forth above, and accordingly, it is required to select the reaction temperature and the time of contact so as to be in accord with such reaction mechanism. In this case, at the first stage for producing the adduct, it is appropriate to effect the reaction by applying a relatively low temperature and a short time of contact; when the temperature is too high and the time of contact is too long at this stage, because the molar ratio of $SO_3$ to fatty acid ester is more than 1.0, the ester linkage of fatty acid ester is cut, resulting in not only a decrease in the yield of α-sulfofatty acid ester but also the generation of undesirable coloring substances as by-products. Therefore, at the first stage in the present invention, the reaction temperature is defined to be in the range of 50° – 85°C and the time of contact is defined to be in the range of 0.5 – 30 seconds: in the case where the reaction temperature is less than 50°C, the speed of producing the adduct becomes extremely low to thereby lower the rate of reacton, while in the case where the reaction temperature is more than 85°C, there take place the cutting of the ester linkage and the generation of coloring substances; and besides, in the case where the time of contact is less than 0.5 second, the adduct cannot be sufficiently produced, while in the case where the time of contact is more than 30 seconds, there take place the cutting of the ester linkage and the generation of coloring substances, so that it is impossible to obtain a product suitable for use as the active ingredient for detergents in these cases.

The second stage in the present invention is a stage where the rearrangement of the adduct produced at the first stage is effected. At this stage, it is required to control the reaction condition lest there should take place any side-reaction. Generally speaking, the higher is the temperature, the quicker is the progress of the arrangement reaction; but in the case where the temperature is more than 150°C, the reaction is attended with the adverse effect of increasing the coloring degree of the product, while in the case where the temperature is less than 95°C, the progress of the rearrangement reaction becomes too slow. As to the time of contact, in the case where it is less than 3 seconds, the rearrangement reaction fails to progress sufficiently, while in the case where it is more than 120 seconds, the coloring degree of the product increases. Therefore, at the second stage in the present invention, the reaction temperature is defined to be in the range of 95° – 150°C and the time of contact is defined to be in the range of 3 – 120 seconds.

According to the present invention, α-sulfofatty acid ester produced through the aforesaid first stage and second stage is neutralized at the third stage. The ester linkage of the α-sulfofatty acid ester in general tends to be cut through hydrolysis when subjected to strong alkalinity with pH value of more than 10, so that, in the case of neutralization with strong alkali, the yield of the intended product salt of α-sulfofatty acid ester is decreased. Meanwhile, in the case where the α-sulfofatty acid ester is subjected to acidity with pH value of less than 6, not only does the coloring degree of the product increase but also there is the possibility that the yield of salt of α-sulfofatty acid ester will decrease as acid hydrolysis affects thereon. Therefore, at the third stage in the present invention, while maintaining the neutralization temperature to be less than 70°C and the pH value to be in the range of 6 – 10, neutralization is effected by adding α-sulfofatty acid ester and an aqueous solution of alkali simultaneously. As the aqueous solution of alkali for use in said neutralization, aqueous solutions of alkali metal hydroxide, ammonia water, ethanol amine, etc. are applicable. In this way, the present invention provides a light-colored salt of α-sulfofatty acid ester in high yield.

The salt of α-sulfofatty acid ester produced by the method of the present invention is useful as the active ingredient for detergents, and it can be employed as said active ingredient for detergent either independently or jointly with other anionic surfactants, nonionic surfactants or amphoteric activator. To cite instances of surfactants which can be used jointly with the present sodium α-sulfofatty acid ester, as the anionic surfactants, there are alkyl benzene sulfonates, α-olefin sulfontes, alcohol sulfates, etc., as the nonionic sulfonates, there are higher alcohol ethoxylates, alkyl phenol ethoxylates, fatty acid polysaccharide esters, etc., and as the amphoteric surfactants, there are amphoteric surfactants of the betaine type, sulfobetaine type and the like. Further, for use in the detergent composition comprising the present sodium α-sulfofatty acid ester, all inorganic and organic builders which have hitherto been prevalently employed are applicable. To cite typical instances of these builders, as the inorganic builder, there are condensed polyphosphates, carbonates, sulfates, borates, etc., and as the organic builder, there are polycarboxylic acid salts, hydroxy polycarboxylic acid salts, starch derivatives, etc.

Hereunder will be given some embodiments of the present invention, but it will be understood that these embodiments do not limit the scope of the present invention.

DESCRIPTION OF THE PREFERRED EMBODIMENTS

EXAMPLE 1

Methyl palmitate was sulfonated by the use of a laboratory continuous falling film type sulfonator made of Pyrex glass and having an inside diameter of 5 mm and an entire length of 1.20 m, said sulfonator consisting of a first reactor section having a length of 40 cm and a second reactor section having a length of 80 cm, each reactor being equipped with a heat retaining device. To be precise, methyl palmitate in the state of a film was made to contact with $SO_3$ gas diluted with nitrogen gas so as to have a concentration of 3% by volume in, while making both run down parallel to each other. The time of contact in this case was set to be 2 seconds for the first reactor section and 6 seconds for the second reactor section, and the molar ratio of $SO_3$ to methyl palmitate was held to be constantly 1.20. And, the effluent from the second reactor section was neutralized with 5% aqueous solution of NaOH under the conditions of the temperature being in the range of 50° – 60°C and the pH value being in the range of 8 – 10.

In the foregoing experiment, the rate of reaction, the color of the product and the content of sodium methyl α-sulfopalmitate in the case where the temperatures of the first and second reactor sections were varied were measured. The results were as shown in the following Table-1. In this connection, the rate of the reaction and the color of product were figured out by applying the following equations, and the content of sodium methyl α-sulfopalmitate was measured through gravimetric analysis.

color of product and the content of sodium methyl α-sulfopalmitate were measured. In this case, as the starting fatty acid ester, methyl palmitate was employed, and the molar ratio of $SO_3$ to methyl palmitate was 1.20, the concentration of $SO_3$ diluted with nitrogen was 3% by volume, the temperature of the first reactor was 70°C, the temperature of the second reac- $$\text{rate of reaction (\%)} = \frac{\text{(number of mole of sodium } \alpha\text{-sulfofatty acid ester + number of mole of sodium salt of } \alpha\text{-sulfofatty acid)}}{\text{number of mole of material fatty acid ester)}} \times 100$$

color = absorbance [5 vol.% aqueous solution of (sodium α-sulfofatty acid ester + sodium salt of α-sulfofatty acid, 420mμ] × 1000

Table-1:

Properties of sodium methyl α-sulfopalmitate according to various reaction temperature

| Experiment No. | Reaction temperature (°C) 1st reactor | Reaction temperature (°C) 2nd reactor | Rate of reaction (%) | Color | Content of sodium methyl α-sulfo-palmitate (%) |
|---|---|---|---|---|---|
| 1 | 40 | 130 | 88.1 | 670 | 74.0 |
| 2 | 50 | 130 | 93.2 | 690 | 82.7 |
| 3 | 70 | 130 | 96.5 | 740 | 91.9 |
| 4 | 80 | 130 | 94.9 | 790 | 88.4 |
| 5 | 100 | 130 | 88.8 | 1300 | 72.8 |
| 6 | 70 | 80 | 85.5 | 550 | 67.7 |
| 7 | 70 | 100 | 91.8 | 640 | 82.3 |
| 8 | 70 | 150 | 95.2 | 970 | 84.2 |
| 9 | 70 | 160 | 93.3 | 3500 | 70.5 |
| * | 70 | 130 | 95.0 | 8700 | 69.8 |

(Remark)
*After blowing a prescribed amount of diluted $SO_3$ gas at 70°C into the material methyl palmitate for 10 minutes to effect batch process reaction, the temperature was raised up to 130°C and aging was conducted for 20 minutes. Subsequently, neutralization was effected by means of 5% NaOH.

As is clear from the showing in Table-1 above, in the case where the temperature of the first reactor was less than 50°C (Experiment No. 1), the rate of reaction became less than 90%, and the content of sodium methyl α-sulfopalmitate was also as low as 74.0%. Also in the case where the temperature of the first reactor was more than 90°C (Experiment No. 5) both the rate of reaction and the content of sodium methyl α-sulfopalmitate lowered, and besides the color deteriorated precipitously. On the other hand, in the case where the temperature of the second reactor was less than 90°C (Experiment No. 6), the rate of reaction and the content of sodium methyl α-sulfopalmitate decreased by a large margin, while in the case where said temperature was more than 150°C (Experiment No. 9), the lowering of the rate of reaction was not so conspicuous, but the color deteriorated sharply, and besides, the content of sodium methyl α-sulfopalmitate decreased. These facts verify that, only in the case where the temperature of the second reactor is set in the range of 90° – 150°C, is it possible to obtain sodium α-sulfofatty acid ester with satisfactory color in high yield.

In this context, Experiment No. 10 is an example of batch process reaction, and in this case the rate of reaction was as high as 95.0%, but the color deteriorated remarkably and the content of sodium methyl α-sulfopalmitate also extremely decreased.

EXAMPLE 2

By varying the time of contact in the first reactor and the second reactor of the same continuous falling film type sulfonator as in Example 1 and applying the same procedures as in Example 1, the rate of reaction, the tor was 130°C, and the same neutralization method as in Example 1 was applied subsequent to sulfonation. The result of this experiment was as shown in the following Table-2.

Table-2:

Properties of sodium methyl α-sulfopalmitate according to various times of contact

| Experiment No. | Time of contact (sec) 1st reactor | Time of contact (sec) 2nd reactor | Rate of reaction (%) | Color | Content of sodium methyl α-sulfo-palmitate (%) |
|---|---|---|---|---|---|
| 11 | 0.2 | 15 | 82.5 | 520 | 82.0 |
| 12 | 0.5 | 15 | 90.1 | 660 | 86.5 |
| 13 | 5 | 15 | 96.4 | 750 | 90.4 |
| 14 | 15 | 15 | 96.2 | 850 | 85.3 |
| 15 | 30 | 15 | 95.4 | 980 | 80.6 |
| 16 | 45 | 15 | 95.3 | 2500 | 74.2 |
| 17 | 5 | 1 | 85.0 | 540 | 69.9 |
| 18 | 5 | 3 | 90.4 | 630 | 80.2 |
| 19 | 5 | 15 | 96.4 | 750 | 90.4 |
| 20 | 5 | 30 | 96.5 | 890 | 89.9 |
| 21 | 5 | 60 | 96.2 | 950 | 85.4 |
| 22 | 5 | 120 | 94.3 | 1100 | 81.0 |
| 23 | 5 | 180 | 94.2 | 4800 | 70.4 |

It is clear from the showing in Table-2 above that only in the case where the time of contact in the first reactor and the second reactor is in the range of 0.5 – 30 seconds and in the range of 3 – 120 seconds, respectively, are the properties of the resulting sodium methyl α-sulfopalmitate satisfactory.

EXAMPLE 3

A series of experiments were conducted by employing the same sulfonator, material and neutralization method as in Example 1. In this case, while maintaining the temperature of the first reactor at 70°C and the temperature of the second reactor at 130°C, the rate of reaction, the color of product and the content of sodium methyl α-sulfopalmitate were measured by applying the same procedures as in Example 1 upon varying the molar ratio of $SO_3$ to methyl palmitate. The results were as shown in the following Table-3.

Table-3:

Properties of sodium methyl α-sulfopalmitate according to various molar ratio of $SO_3$

| Experiment No. | Molar ratio of $SO_3$ to methyl palmitate | Rate of reaction (%) | Color | Content of sodium methyl α-sulfo-palmitate (%) |
|---|---|---|---|---|
| 24 | 0.9 | 85.4 | 620 | 88.1 |
| 25 | 1.0 | 90.7 | 680 | 88.4 |
| 26 | 1.2 | 96.5 | 740 | 91.9 |
| 27 | 1.4 | 93.6 | 980 | 85.1 |
| 28 | 1.5 | 92.9 | 1100 | 81.4 |

Table-3:-continued

| Experiment No. | Molar ratio of $SO_3$ to methyl palmitate | Rate of reaction (%) | Color | Content of sodium methyl α-sulfo-palmitate (%) |
|---|---|---|---|---|
| 29 | 1.6 | 92.6 | 2900 | 72.5 |

As is clear from the showing in Table-3 above, in the case where the molar ratio of $SO_3$ to methyl palmitate is less than 1.0, the color of the product is satisfactory, but the rate of reaction decreases precipitously, while in the case where said molar ratio is more than 1.5, the rate of reaction becomes more than 90%, but the color of the product precipitously deteriorates and the content of sodium methyl α-sulfopalmitate also decreases.

EXAMPLE 4

Methyl hydrogenated tallow fatty acid ester was sulfonated by the use of a continuous falling film type sulfonator made of stainless steel having an inside diameter of 40 mm and a total length of 1.5 m, said sulfonator consisting of a first reactor section having a length of 60 cm and the second reactor section having a length of 90 cm, each reactor being equoipped with a heat retaining device. At the time of sulfonation, the temperature of the first reactor section was held at 70°C and the temperature of the second reactor section at 130°C, the feed of the material was set to be 50 Kg/hr, the concentration of $SO_3$ (as diluted with dry air) was set to be 6% by volume, the molar ratio of $SO_3$ to methyl hydrogenated tallow fatty acid ester was set to be 1.2, and the time of contact was set to be 5 seconds for the first reactor section and 10 seconds for the second reactor section.

When neutralization of the resulting sulfonation product was effected under the condition of the temperature being in the range of 40° – 50°C and the pH value being in the range of 6 – 10 by adding sulfonic acid obtained under the foregoing sulfonation conditions and 5% aqueous solution of NaOH simultaneously thereto, there was obtained sodium methyl α-sulfo hydrogenated tallow fatty acid ester having the following properties. In this connection, the rate of reaction, the color and the content was measured by applying the same procedures as in Example 1.

rate of reaction: 95.8%, color: 740, content: 89.8%

This sodium methyl α-sulfo hydrogenated tallow fatty acid ester demonstrated a satisfactory efficiency as the surface active agent for use in detergents.

EXAMPLE 5

Under the same conditions for sulfonation/neutralization as in Example 1, by employing methyl palm fatty acid ester as the material, sulfonation was effected. The properties of the starting resulting sodium α-sulfofatty acid ester as measured by applying the same procedures as in Example 1 were almost equal to that in Example 4, that is, the rate of reaction was 95.7%, the color was 750, and the content was 90.5%.

EXAMPLE 6

By making stearic acid react with methanol, ethanol, isopropanol and n-butanol, respectively, the methyl ester, ethyl ester, isopropyl ester and butyl ester of stearic acid were respectively synthesized. After sulfonating these esters by applying the same conditions for sulfonation as in Experiment No. 3 of Example 1, neutralization was effected by the same method as in Example 1. When the properties of each product thus obtained were measured by applying the same procedures as in Example 1, the results were as shown in the following Table-4.

Table-4:

| Stearic acid ester | Rate of reaction (%) | Color | Content of sodium α-sulfo-stearic acid ester (%) |
|---|---|---|---|
| -methyl | 95.8 | 800 | 90.9 |
| -ethyl | 95.3 | 720 | 89.7 |
| -isopropyl | 95.6 | 760 | 90.5 |
| -butyl | 95.1 | 740 | 90.6 |

As is clear from the showing in Table-4 above, each salt of α-sulfostearic acid ester was satisfactory in respect of the rate of reaction, the color and the content.

EXAMPLE 7

After sulfonating methyl palmitate under the same conditions for sulfonation as in Experiment No. 3 of Example 1, neutralization of the resulting sulfonation product was effected by applying such modes as shown in the following Table-5. When the properties of each sodium methyl α-sulfopalmitate thus obtained were measured by applying the same procedures as in Example 1, the results were as shown in Table-5.

Table-5:

| Mode of neutralization | Rate of reaction (%) | Color | Content of sodium methyl α-sulfo-palmitate (%) |
|---|---|---|---|
| By adding sulfonic acid to aqueous solution of alkali (50°–60°C) | 96.2 | 760 | 65.2 |
| By adding aqueous solution of alkali to sulfonic acid (50–60°C) | 96.4 | 750 | 72.3 |
| By simultaneously mixing while retaining pH value in the range of 6–10 (80°C) | 96.4 | 770 | 76.5 |
| By simultaneously mixing while retaining pH value in the range of 8–10 (50–60°C) | 96.5 | 740 | 91.9 |

As is clear from the showing in Table-5 above, the content of sodium methyl α-sulfopalmitate becomes more than 80% only in the case where sulfonation is effected while retaining the pH value in the range of 6 – 10 and the temperature in the range of 50° –60°C (in the case where said aqueous solution of alkali and sulfonic acid are simultaneously mixed); according to other methods of neutralization, it always becomes less than 80%, rendering the product unfit for use as the surface active agent for detergent.

What is claimed is:

1. A process for preparing a salt of an α-sulfofatty acid ester by sulfonating and then neutralizing a fatty acid ester having the formula RCH$_2$COOR', wherein R is alkyl having 8 to 18 carbon atoms and R' is alkyl having one to 5 carbon atoms, which comprises the steps of:
   1. flowing a film of said fatty acid ester through a first reaction zone and contacting said film with an SO$_3$-inert gas mixture containing one to 15 percent by volume of SO$_3$, at a molar ratio of SO$_3$ to said fatty acid ester of from 1.0 to 1.5, at a first reaction temperature of from 50° to 85°C, and for a first contact time of from 0.5 to 30 seconds, to form an intermediate sulfonated reaction product,
   2. flowing a film of said intermediate reaction product from step 1 through a second reaction zone and contacting the latter film with said SO$_3$-inert gas reaction mixture, at a second reaction temperature of from 95° to 150°C, and for a second contact time of from 3 to 120 seconds, to form an α-sulfofatty acid ester reaction product, and
   3. immediately neutralizing the reaction product of step 2 by mixing said reaction product of step 2 with a neutralizing agent selected from the group consisting of an aqueous solution of an alkali metal hydroxide, aqueous ammonia and an ethanol amine, at a neutralization temperature at less than 70°C and at a pH of from 6 to 10, to obtain a neutralized product containing at least 80 percent by weight of a salt of said α-sulfofatty acid ester having a low color value.

2. A process as claimed in claim 1 in which steps 1 and 2 are carried out in a single reactor by continuously flowing a film of said fatty acid ester downwardly from the top of the reactor in contact with a parallel-flowing stream of said SO$_3$-inert gas mixture through two reaction zones in said reactor in series, and wherein the length of the second reaction zone is greater than the length of the first reaction zone.

3. A process as claimed in claim 1, in which said second contact time is longer than said first contact time.

4. A process as claimed in claim 1, in which R is alkyl having 10 to 16 carbon atoms and R' is alkyl having 1 to 2 carbon atoms.

5. A process as claimed in claim 4, in which the SO$_3$-inert gas mixture contains from 2 to 10 percent by volume of SO$_3$.

6. A process as claimed in claim 5, in which the neutralization temperature is from 50° to 60°C, and the pH range is from 8 to 10.

7. A process as claimed in claim 6, in which the neutralizing agent is an aqueous solution of sodium hydroxide.

8. A process as claimed in claim 1 in which said fatty acid ester is derived from a natural fat having an iodine number of less than one.

* * * * *